United States Patent
Pedersen et al.

(10) Patent No.: US 10,703,752 B2
(45) Date of Patent: Jul. 7, 2020

(54) INTEGRIN ANTAGONISTS

(71) Applicant: OXURION NV, Leuven (BE)

(72) Inventors: Ove Pedersen, Leuven (BE); Elke Vermassen, Leuven (BE)

(73) Assignee: OXURION NV, Leuven (BE)

( * ) Notice: Subject to any disclaimer, the term of this patent is extended or adjusted under 35 U.S.C. 154(b) by 0 days.

(21) Appl. No.: 16/544,259

(22) Filed: Aug. 19, 2019

(65) Prior Publication Data

US 2020/0055849 A1 Feb. 20, 2020

(30) Foreign Application Priority Data

Aug. 17, 2018 (EP) ..................................... 18189615
Sep. 13, 2018 (EP) ..................................... 18194258

(51) Int. Cl.
*C07D 471/04* (2006.01)
*A61K 9/00* (2006.01)

(52) U.S. Cl.
CPC .......... *C07D 471/04* (2013.01); *A61K 9/0019* (2013.01)

(58) Field of Classification Search
CPC .................................................... C07D 471/04
USPC .......................................... 544/328; 514/256
See application file for complete search history.

(56) References Cited

U.S. PATENT DOCUMENTS

| | | | | |
|---|---|---|---|---|
| 7,825,119 | B2 * | 11/2010 | Lefrancois | C07D 401/14 514/252.02 |
| 2006/0052398 | A1 | 3/2006 | Ruxer et al. | |
| 2008/0058348 | A1 | 3/2008 | Lefrancois et al. | |

FOREIGN PATENT DOCUMENTS

| | | |
|---|---|---|
| WO | 2011/094285 A1 | 8/2011 |
| WO | 2011/119282 A1 | 9/2011 |
| WO | 2015/175954 A1 | 11/2015 |

OTHER PUBLICATIONS

Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharnn. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2, p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*
Wang et al., "Novel Targets, etc.," Curr Diab Rep 12:355-363. (Year: 2012).*
Tolentino et al., "Current and, etc.," Expert Opinion on Investigational Drugs, 25(9), 1011-1022. (Year: 2016).*
Pearce et al., Failure modes in anticancer drug discovery and development, Cancer Drug Design and Discovery Edited by Stephen Neidle, Chapter 18, pp. 424-435. (Year: 2008).*
Goel et al., "Integrins in, etc.," Endrocrine-Related Cancer, 15, 657-664. (Year: 2008).*
Simone, Oncology:Introduction, Cecil Textbook of Medicine, ed Bennett et al. W.B.Saunders CO. 20th ed, vol. 1, pp. 1004-1010. ( Year: 1996).*
Gura, Systems for identifying New Drugs Are Often Faulty, Cancer Models, Science, vol. 278, No. 5340, pp. 1041-1042, Nov. 1997. (Year: 1997).*
Johnson et al., Relationships between drug activity in NCI preclinical in vitro and in vivo models and early clinical trials, British Journal of Cancer,64(10): 1424-1431. (Year: 2001).*
Mahabeleshar et al., Angiogenesis, etc., Semin. Oncol, 34:555-565. (Year: 2007).*
Robinson et al., "The role of, etc.," Current Opinion in Cell Biology, 23:630-637. (Year: 2011).*
Naci et al., "Alpha2beta 1, etc.,":Seminars in Cancer Biology 35, 145-153. (Year: 2015).*
Zhao-He et al., "Roles of integrin, etc.," Chin. J. Nat. Med., 17(4) 241-251. (Year: 2019).*
European Search Report and Written Opinion dated Feb. 15, 2019, issued in corresponding European Application No. 18 19 4258, filed Sep. 13, 2018, 8 pages.
European Search Report and Written Opinion dated Feb. 18, 2019, issued in corresponding European Application No. 18 18 9615, filed Aug. 17, 2018, 5 pages.
Hajnal, K., et al., "Prodrug Strategy in Drug Development," Acta Medica Marisiensis 62(3):356-362, 2016.

* cited by examiner

*Primary Examiner* — Patricia L Morris
(74) *Attorney, Agent, or Firm* — Christensen O'Connor Johnson Kindness PLLC

(57) ABSTRACT

The present invention relates to novel integrin antagonists of Formula I and their use as a medicament, in particular for inhibiting neovascularization.

5 Claims, 1 Drawing Sheet

INTEGRIN ANTAGONISTS

FIELD OF INVENTION

This present invention relates to novel integrin antagonists and the use of these compounds as a medicament, in particular for inhibiting neovascularization.

BACKGROUND OF THE INVENTION

Diabetic macular edema (DME) is an accumulation of fluid in the macula of patients with diabetic retinopathy (DR), which can occur at any stage of the disease. DR is one of the most common microvascular complications of diabetes. Vision-threatening DR (i.e. DME and proliferative diabetic retinopathy (PDR) is the leading cause of visual disability and blindness among working-aged adults around the world. Globally, the overall prevalence of DR is estimated at 34.6% of the people with diabetes, while the overall prevalence of DME is estimated at approximately 20% of the people with DR (Yau et al., 2012). The prevalence of DME is expected to rise further due to the increasing prevalence of diabetes, ageing of the population and increased life expectancy of people with diabetes: the number of adults with diabetes worldwide was estimated at 425 million in 2017 and is expected to increase to 629 million by 2045.

Although the exact mechanisms by which diabetes causes retinopathy remains unclear, several studies have shown the elevation of reactive oxygen species, advanced glycation end products and circulating and vitreous cytokines and chemokines in relation to the disease. Inflammation in the retina is a major early pathological hallmark of DR. Inflammatory and vasodilator factors can modify endothelial function, leading to blood-retinal barrier breakdown, which results in accumulation of plasma proteins and lipids into the macula. When the thickening involves the fovea or threatens to involve the fovea, the patient becomes symptomatic with metamorphopsia and vision loss.

The interaction between the vitreous and the retina has been found to be involved in the development of macular edema. In particular, when the vitreous and the macular area of the retina are tightly conjugated, macular edema can be greatly promoted. Among patients with DR, DME was present only in 20% of patients with posterior vitreous detachment (PVD) as compared to in 55% of patients without PVD, suggesting a strong protective effect of PVD. The proposed mechanism for potential benefit of PVD is the relief of vitreomacular traction, however, both transvitreal oxygenation and improved growth factor diffusion (away from the pre-macular hyaloid) have also been suggested to potentially have beneficial effects.

Good control of blood glucose, blood pressure and blood lipids is essential and can delay the onset of DR and slow its progression. Treatment occurs in some cases by focal/grid laser photocoagulation using small, light-intensity laser burns (50-100 µm) to micro-aneurisms or diffuse areas of thickening. However, this treatment could result in complications such as loss of central vision, central scotomas and decreased color vision. More recently, subthreshold micropulse laser has been developed as a treatment that theoretically avoids damaging the inner neurosensory retina, thereby reducing potential complications.

Several pharmacologic agents are now available for the treatment of DME, including anti-vascular endothelial growth factor (VEGF) agents and corticosteroids. VEGF is a potent vasopermeability factor contributing to the macular thickening and visual impairment associated with DME. Anti-VEGF compounds decrease angiogenesis and vascular permeability, causing regression of neovascularization and reduction of edema. Several clinical studies have shown that anti-VEGF treatment is more effective than focal/grid laser treatment at decreasing central subfield thickness (CST) and improving vision in DME patients. Adverse events (AEs) related to anti-VEGF treatment are rare and mostly related to the need for repeated intravitreal (IVT) injections over a prolonged period of time.

Inflammation plays an important role in the pathogenesis of DME. Cytokines and chemokines released by leukocytes in the blood significantly increase vascular permeability leading to more fluid build-up under the retina. Corticosteroid therapies can inhibit inflammatory mediators. Several clinical studies have shown that corticosteroids are effective in decreasing CST and improving vision in DME. While the treatment burden of corticosteroid implants is much lower than that of anti-VEGF agents, intraocular corticosteroids are associated with increased risks of cataract development and elevation of intraocular pressure. Overall, the use of IVT corticosteroids in patients with DME is therefore reserved as a second-line therapy in those who respond poorly to IVT anti-VEGF therapy and is contraindicated in patients with underlying glaucoma.

Of the possible treatments of DME mentioned above, the anti-VEGF agents are currently the first-line gold standard treatment for DME. Most studies to date however report that a substantial proportion of DME patients, up to 40%, have persistent edema and loss of visual acuity despite anti-VEGF treatment. These findings suggest that other pathways, independent of VEGF, contribute to the development of DME, and there is thus an important clinical need for additional effective treatments for DME.

Integrins constitute a family of transmembrane cell surface receptors that can mediate cell-cell and cell-extracellular matrix interactions. Integrins are involved in various biological processes including cell differentiation, adhesion, shape, migration, motility, invasion, proliferation, and survival. Because of their role in these biological processes, integrins have also been associated with various pathological conditions, such as cancer and ophthalmic disorders. In the eye, integrins have been shown to play an important role in neovascularization, vascular permeability and vitreoretinal adhesion.

Integrins are obligate heterodimeric receptors consisting of a non-covalently bound $\alpha$ and $\beta$ subunit. Different combinations of the 18 $\alpha$ and the 8 $\beta$ known subunits constitute the family of 24 heterodimeric integrin members recognized thus far. The integrin family of receptors can be broadly classified into 4 different categories depending on their ligand recognition pattern: 1) the tripeptide L-arginine-glycine-aspartic acid (RGD) binding, 2) collagen binding, 3) laminin binding and 4) leukocyte binding types of integrins.

Interaction of integrins with the extracellular matrix can lead to neovascularization of the retinal surface, which can eventually extend towards the vitreous region. Immunohistological staining on human retinal tissues derived from PDR patients has shown that actively proliferating vascular endothelial cells express the integrins $\alpha_v\beta_3$ and $\alpha_v\beta_5$, which are not highly expressed in quiescent endothelial cells (Friedlander et al., 1996; Ning et al., 2008). In addition, $\alpha_v\beta_3$ and $\alpha_{IIb}\beta_3$ have been shown to be expressed in fibrovascular epiretinal membranes from patients with active PDR in the fibrotic stage (Ning et al., 2008; Abu El-Asrar, Missotten and Geboes, 2010), whereas $\alpha 5\beta 1$ has been shown to be overexpressed in a laser-induced mouse model of CNV (Umeda et al., 2006). In line with this, several non-clinical studies have demonstrated that inhibition of integrins attenuates leukostasis and retinal vascular permeability (Santulli et al., 2008; Iliaki et al., 2009; Rao et al., 2010). Antagonism of $\alpha_v\beta_3$ and $\alpha_v\beta_5$ prevented retinal neovascularization but did not harm pre-existing blood vessels (Friedlander et al., 1996; Hammes et al., 1996; Lahdenranta et al., 2007; Santulli et al., 2008), whereas inhibition of $\alpha_5\beta_1$ inhibited endothelial cell proliferation and produced regression of choroidal neovascular membranes in different animal models (Ramakrishnan et al., 2006; Umeda et al., 2006).

The RGD motif is very commonly found in many components of the extracellular matrix, including vitronectin, fibronectin and fibrinogen. Integrins are therefore heavily linked to extracellular matrix proteins, thereby mediating cell-extracellular matrix adhesion, for instance in the vitreoretinal interface. Analogues of the RGD motif are known to compete for the RGD motif of extracellular matrix proteins to disrupt integrin-extracellular matrix interactions and therefore loosen the attachments in in vitro experiments (Gehlsen et al., 1988; Pierschbacher and Ruoslahti, 1987; Zhou, Zhang and Yue, 1996). In line with this, IVT injection of soluble RGD peptides has been shown to induce PVD in rabbit eyes (Oliveira et al., 2002). Moreover, in humans, 3 IVT injections of the integrin antagonist ALG 1001 (Allegro Ophthalmics, LLC) have been shown to induce total PVD in 6 of 11 DME patients with no or partial PVD at baseline in an initial proof-of-concept study (Kuppermann, 2013; Boyer et al., 2014).

These observations underpin the preference for using a pan-integrin antagonist that targets the different types of integrins that underlie different aspects of the disease to be treated, most notably $\alpha_v\beta_3$, $\alpha_v\beta_5$ and $\alpha_5\beta_1$. The complexity is that such pan-integrin antagonists will often also antagonize other RGD-binding integrins, which may cause side effects. Most notable is the platelet integrin, $\alpha_{IIb}\beta_3$, whose antagonism may interfere with platelet activation and aggregation.

Patent application publications WO2011/119282 A1, WO2011/094285 A1, US2006/0052398 A1 and US2008/058348 A1 disclose compounds as potential integrin antagonists or as potential vitronectin receptor antagonists. The compounds disclosed in these patent applications can be summarized as generally corresponding to Formula A

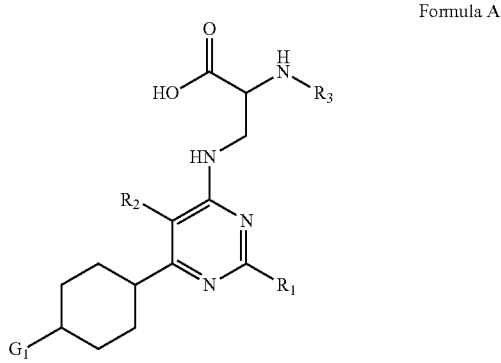

Formula A wherein, generally $G_1$ represents a substituted pyridine or tetrahydro naphtyridine, $R_1$ and $R_2$ are hydrogen, methyl or ethyl, and $R_3$ is a hydrophobic tail group. In particular, in the exemplified compounds with confirmed activity, $R_3$ comprises an alkyl, cycloalkyl or (hetero)aromatic end group.

There is a need for novel integrin antagonists, in particular integrin antagonists that act simultaneously on the different types of integrins that are involved in disease pathways, such as $\alpha_v\beta_3$, $\alpha_v\beta_5$ and $\alpha_5\beta_1$, but which have a reduced risk of interfering with platelet aggregation through their effect on $\alpha_{IIb}\beta_3$.

SUMMARY OF THE INVENTION

The present invention provides compounds according to formula (I) or the pharmaceutically acceptable salt, pharmaceutically acceptable solvate, isomer or mixture thereof,

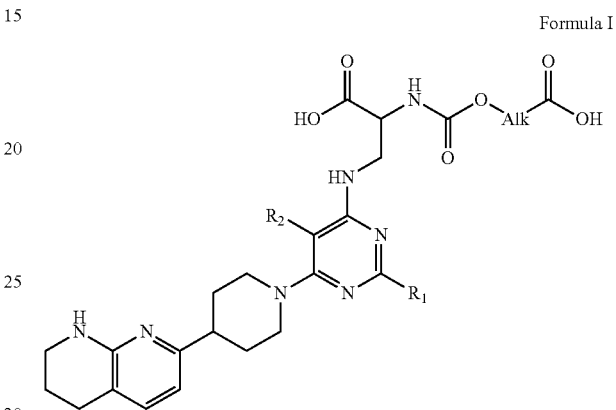

Formula I wherein
$R_1$ and $R_2$ are independently selected from the group consisting of hydrogen, methyl or ethyl; and
Alk is $C_{1-4}$alkylene.

The present invention further relates to a pharmaceutical composition comprising the compound of the present invention, and one or more pharmaceutically acceptable carries.

The present invention further relates to compounds for use as a medicament. A further objective of the present invention is to provide compounds to inhibit pathological neovascularization.

The present invention further relates to compounds for use in the treatment and/or prevention of ophthalmic disorders, such as diabetic macular edema and diabetic retinopathy.

DETAILED DESCRIPTION OF THE INVENTION

Figure 1:
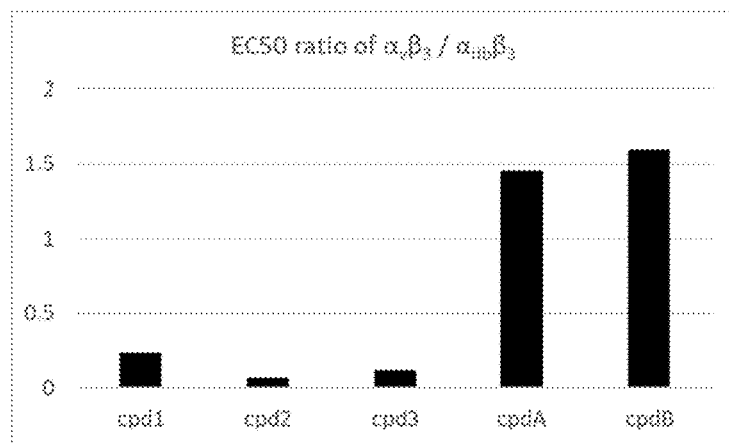
FIG. 1 Shows EC50 ratios for cpd1, cpd2, cpd3 and comparative compounds cpdA and cpdB for integrin $\alpha_v\beta_3$ over $\alpha_{IIb}\beta_3$ (lower values indicate a higher specificity for ($\alpha_v\beta_3$).

It is further understood that all definitions and preferences as described for the compounds of the invention above equally apply for this embodiment and all further embodiments, as described below.

As used in the foregoing and hereinafter, the following definitions apply unless otherwise noted.

The term "alkylene", alone or in combination means an alkane-derived diradical, which may be a straight chain alkylene or branched alkylene, containing from 1 to 4 carbon atoms. The straight chain or branched alkylene group is attached at any available point to produce a stable compound. According to certain embodiments $C_{A-B}$ alkylene defines a straight or branched alkylene diradical having from A to B carbon atoms, e.g. $C_{1-4}$ alkylene defines a straight or branched alkylene diradical having from 1 to 4 carbon atoms, such as for example methylene, ethylene, 1-propylene, 2-propylene, I-butylene, 2-butylene, 2-methyl-1-propylene.

Where reference is made to percentages, this refers to weight to weight percentages, unless the context clearly dictates otherwise.

As described herein before, the present invention provides compounds according to formula (I) or a pharmaceutically acceptable salt, pharmaceutically acceptable solvate, isomer or mixture thereof,

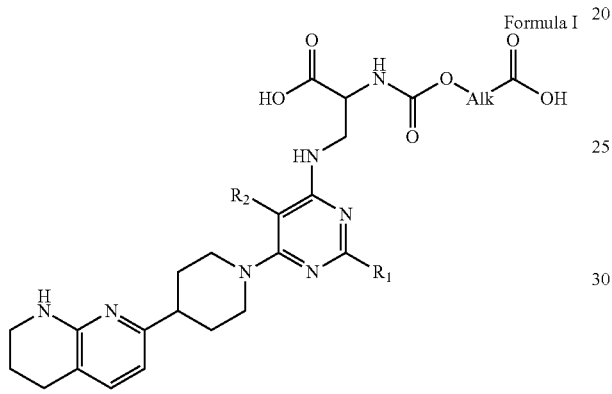

Formula I wherein $R_1$ and $R_2$ are independently selected from the group consisting of hydrogen, methyl or ethyl; and Alk is $C_{1-4}$alkylene.

According to a certain embodiment of the present invention, either $R_1$ and $R_2$ are both methyl, or $R_1$ is hydrogen and $R_2$ is ethyl.

According to a preferred embodiment, the present invention provides those compounds wherein $R_1$ and $R_2$ are both methyl.

According to a certain embodiment of the present invention, Alk is $C_{1-2}$ alkylene.

According to a preferred embodiment of the present invention, the compound is selected from the group consisting of

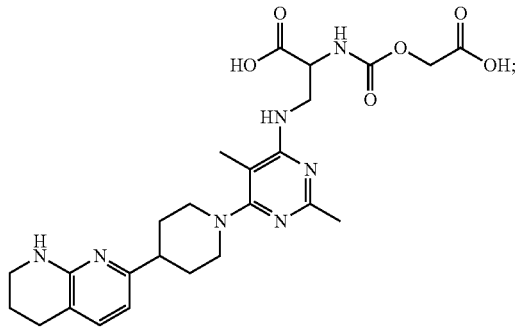

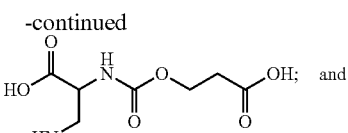

and

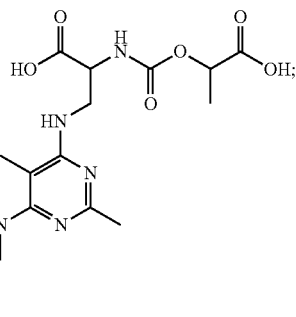

or a pharmaceutically acceptable salt, pharmaceutically acceptable solvate, isomer or mixture thereof.

The compound of the present invention, as detailed above, may have a center of chirality and exists as stereochemically isomeric forms. The term "stereochemically isomeric forms" as used herein defines all the possible compounds made up of the same atoms bonded by the same sequence of bonds but having different three-dimensional structures which are not interchangeable, which the anti-inflammatory compound as specified herein, may possess.

Unless otherwise mentioned or indicated, the chemical designation of the compounds, as detailed above, encompasses the mixture of all possible stereochemically isomeric forms, which said compounds may possess. Said mixture may contain all diastereomers and/or enantiomers of the basic molecular structure of said compounds for use. All stereochemically isomeric forms of the compounds of the present invention both in pure form or mixed with each other are intended to be embraced within the scope of the present invention.

In a preferred embodiment, the present invention provides the (S) enantiomeric forms of the compounds according to Formula I. Therefore, in a particular embodiment, the present invention provides a compound according to Formula II,

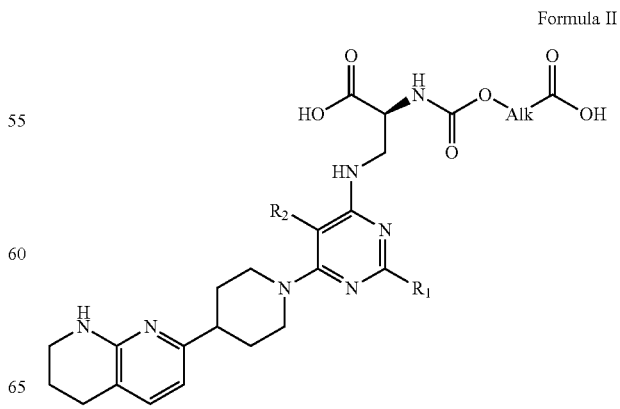

Formula II wherein $R_1$, $R_2$ and Alk are as defined in the application.

In a further embodiment, the present invention provides a compound selected from the group consisting of

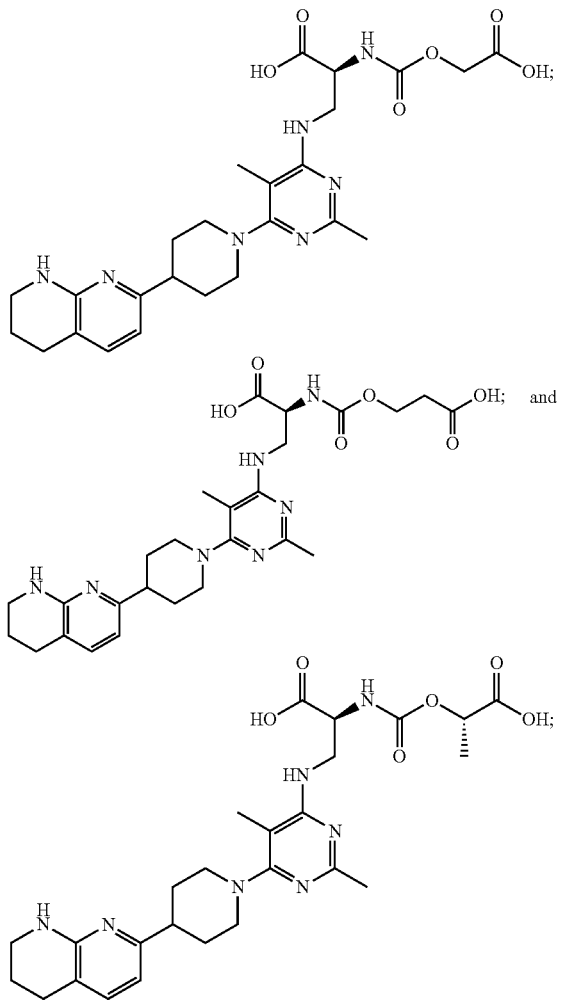

or a pharmaceutically acceptable salt, pharmaceutically acceptable solvate, isomer or mixture thereof.

For therapeutic use, salts of the compounds for use of the present invention, as detailed above, are those wherein the counter-ion is pharmaceutically acceptable, which salts can be referred to as pharmaceutically acceptable acid and base addition salts. However, salts of acids and bases that are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove are meant to comprise the therapeutically active non-toxic acid and base addition salt forms that the compounds for use of the present invention, as detailed above, are able to form. The pharmaceutically acceptable acid addition salts can conveniently be obtained by treating the base form with such appropriate acid in an anion form. Appropriate anions comprise, for example, trifluoroacetate, acetate, benzenesulfonate, benzoate, bicarbonate, bitartrate, bromide, calcium edetate, camsyiate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and the like. The counterion of choice can be introduced using ion exchange resins. Conversely said salt forms can be converted by treatment with an appropriate base into the free base form. A preferred salt is the hydrochloride salt of the compounds described herein.

The compounds for use as specified herein, containing an acidic proton may also be converted into their nontoxic metal or amine addition salt forms by treatment with appropriate organic and inorganic bases in a cation form. Appropriate basic salts comprise those formed with organic cations such as benzathine, chloroprocaine, choline, diethanolamine, ethylenediamine, meglumine, procaine, and the like; and those formed with metallic cations such as aluminum, calcium, lithium, magnesium, potassium, sodium, zinc, and the like. Conversely said salt forms can be converted by treatment with an appropriate acid into the free form.

The term addition salt as used hereinabove also comprises the solvates which the compounds for use, as specified herein, as well as the salts thereof, are able to form. Such solvates are for example hydrates, alcoholates and the like.

As will be understood from the disclosures herein, the current invention particularly provides isolated compounds and isolated compositions. Compounds are in particular obtained by in vitro synthesis, such as by chemical synthesis. In a further embodiment, compounds of the invention have a purity of at least 85%, in particular at least 90%, more in particular at least 95%. In a particular embodiment, the present invention provides a method for providing a compound of the invention, the method comprising chemically synthesizing the compound of the invention and packaging the synthesized compound in a sterile container. In a further embodiment, the present invention provides a method for providing a compound of the invention, the method comprising chemically synthesizing the compound at a purity of at least 85%, in particular at least 90%, more in particular at least 95%. Preferably, the synthesized compound is subsequently packaged in a sterile container.

Compositions

The present invention further relates to a pharmaceutical composition, the composition comprising a compound as defined above and as defined in any one of the embodiments presented herein.

In the rest of the text, the expression "compound" or "compound according to the invention" is understood, for the purposes of the present invention, both in the plural and the singular, that is to say that the inventive composition may comprise one or more than one "compound according to the invention".

In a particular embodiment, the present invention provides a pharmaceutical composition comprising the compound according to any one of the claims, and one or more pharmaceutically acceptable carriers. Examples of pharmaceutically acceptable formulations as well as methods for making them can be found, e.g., in Remington's Pharmaceutical Sciences (e.g. 20th Edition; Lippincott, Williams & Wilkins, 2000) or in any Pharmacopeia handbook (e.g. US-, European- or International Pharmacopeia).

In another embodiment, the present invention provides a composition comprising an aqueous buffer wherein a compound of the invention has been dissolved. In a further embodiment, the present invention provides a pharmaceutical composition comprising an aqueous buffer wherein a compound of the invention and one or more pharmaceutically acceptable carriers have been dissolved. In another further embodiment, the present invention provides a pharmaceutical composition consisting of an aqueous buffer, a compound of the invention and one or more pharmaceutically acceptable carriers.

In a particular embodiment, the present invention provides a composition comprising an integrin antagonist, wherein at least 90% of the integrin antagonist compounds of the composition is a compound according to the invention. Preferably at least 95%, especially at least 99% of the integrin antagonist compounds of the invention is a compound according to the invention. In another particular embodiment, the compositions of the invention are substantially free of another integrin antagonist, such as compound A. In a further embodiment, the ratio of the compound of the invention over other integrin antagonist compounds, such as compound A, is more than 98:2, particularly more than 99:1, more particularly more than 99.9:0.1. In yet another embodiment, the present invention provides a composition as described herein, wherein the composition is substantially free of compound A, in particular wherein the composition comprises less than 3%, especially less than 2%, preferably less than 1% of compound A, more in particular with the proviso that the composition does not comprise compound A.

In another embodiment, the current invention provides a composition comprising a first active ingredient and a second active ingredient, wherein the first active ingredient is an integrin antagonist according to the invention, and wherein the composition is substantially free of an integrin antagonist other than the first active ingredient. In a further embodiment, the second active ingredient is a compound that binds to and inhibits the activity of VEGF or a VEGF receptor.

Integrin antagonist or integrin antagonist compound in the current application preferably refers to a compound having a half maximal effective concentration (EC50) against integrin receptors of less than 1 μM, in particular an EC50 against the $α_vβ_3$ integrin receptor. Suitable methods for determining EC50 values are known to the skilled person. One particular method to determine the value for a particular compound is a competition ELISA assay wherein the integrin receptor under investigation (in particular human $α_vβ_3$ integrin receptor) is coated to a multi-well plate using a 4 μg/mL solution and the wells are blocked with 5% bovine serum albumin. The fibronectin concentration to be used in the assay is determined experimentally in a separate experiment by testing the binding of various fibronectin concentrations to the coated integrin under investigation, the concentration of fibronectin for the assay being the one that gives 80% of maximal binding. The determined concentration of human fibronectin is then added to the coated and blocked wells in the presence of increasing concentrations of the compound. After 2 h incubation at 37° C., the wells are washed and the bound fibronectin is detected with the help of a specific reagent, such as a detectable anti-fibronectin antibody. Quantitative analysis of the data is then performed to determine EC50 values, i.e. the concentration of the compound that reduces fibronectin binding to the coated receptor by 50%.

In another embodiment, the present invention provides a composition comprising an aqueous buffer and a compound of the invention. In a further embodiment, the present invention provides a pharmaceutical composition comprising an aqueous buffer, a compound of the invention and one or more pharmaceutically acceptable carriers. In another further embodiment, the present invention provides a pharmaceutical composition consisting of an aqueous buffer, a compound of the invention and one or more pharmaceutically acceptable carriers.

In a particular embodiment, the present invention provides a composition comprising between 0.1 and 1000 mg of a compound of the invention per ml of the composition, in particular between 1 and 500 mg/ml, more in particular between 1 and 100 mg/ml. In a further embodiment, the composition comprises between 10 and 100 mg/ml, such as between 20 and 75 mg/ml.

Compounds and/or Compositions for Use as a Medicament

The present invention further relates to a compound for use as a medicament.

In a particular embodiment, the present invention relates to a compound for use in inhibiting neovascularization.

In a further embodiment, the present invention relates to a compound for use in the treatment and/or prevention of cancer. In particular, for inhibiting cancer growth and/or metastasis.

In another embodiment, the present invention relates to a compound for use in the treatment and/or prevention of an ophthalmic disorder. In particular for treating and/or preventing neovascularization in the eye. More in general, the present invention provides pharmaceutical compounds and compositions for treating, reducing, ameliorating, or inhibiting the progression of, (pathological) ocular neovascularization. In another aspect, the present invention provides pharmaceutical compounds and compositions for treating, reducing, ameliorating, or inhibiting the progression of, an ophthalmic disorder resulting from, or having an etiology in, ocular neovascularization.

In a further embodiment, the present invention relates to a compound for use in the treatment and/or prevention of ophthalmic disorders, wherein said ophthalmic disorder is selected from the group consisting of wet age-related macular degeneration, retinal detachment, posterior uveitis, corneal neovascularization, iris neovascularization, diabetic macular edema, and diabetic retinopathy.

In yet another embodiment, the compounds of the invention are provided for use as an integrin antagonist, in particular a vitronectin receptor antagonist, in vitro or in vivo. In a particular embodiment, the integrin is an RGD-binding integrin. In a further embodiment, the integrin is an integrin comprising an $α_v$, $α_5$ or $α_8$ subunit. In a more particular embodiment, the integrin is an $α_vβ_3$, $α_vβ_5$ or $α_5β_1$ receptor.

In another embodiment, the compounds of the invention are for use in reducing vascular permeability, preferably for reducing retinal vascular permeability. In a further embodiment, the compounds for the invention are for use in the treatment and/or prevention of edema, in particular macular edema, more in particular diabetic macular edema.

In another embodiment, the compounds of the invention are provided for use in inducing posterior vitreous detachment (PVD). In another embodiment, the compounds of the invention are provided for use in the treatment of vitreomacular traction.

As mentioned before, the present invention relates to novel compounds, their pharmaceutically acceptable salts, pharmaceutically acceptable solvates, isomers or mixtures thereof. The compound of the present invention may also be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, by parenteral or intravitreal injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets.

It is especially advantageous to formulate the aforementioned compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

In one particular embodiment, the present invention provides a package comprising a compound of the invention, and a leaflet with instructions to administer the compound to a patient having an ophthalmic disorder as listed herein, in particular a patient having wet age-related macular degeneration, diabetic retinopathy or diabetic macular edema, more in particular diabetic retinopathy or diabetic macular edema.

For performing the treatment and/or prevention, the compounds or the compositions as described herein may be administered to a patient by any method that leads to delivery of the therapeutic agent to the site of the ophthalmic condition, such as by administration to the eye. In another embodiment, the use, treatment and/or prevention comprises contacting the vitreous and/or aqueous humour with an effective amount of a composition comprising a compound of the invention. Administration may be by an ocular route, such as topical, subconjunctival, sub-Tenon, intraocular, ocular implants, etcetera. Topical administration may comprise administration of one or a few drops of a composition comprising a compound of the invention to the eye. Delivery to areas within the eye, in situ can be accomplished by injection, cannula or other invasive device designed to introduce precisely metered amounts of a desired ophthalmic composition to a particular compartment or tissue within the eye (e.g. posterior chamber or retina). An intraocular injection may be into the vitreous (intravitreal), or under the conjunctiva (subconjunctival), or behind the eye (retrobulbar), into the sclera, or under the Capsule of Tenon (sub-Tenon). Other intraocular routes of administration and injection sites and forms are also contemplated and are within the scope of the invention. In a preferred embodiment, the treatment and/or prevention comprises administration of the compound by intravitreal injection. Preferably this is performed through self-sealing gauge needles or other any suitably calibrated delivery device. Injection into the eye may be through the pars plana via the self-sealing needle.

When administering the composition by intravitreal injection, the active agents should be concentrated to minimize the volume for injection. Preferably, the volume for injection is less than about 5 mL. Volumes such as this may require compensatory drainage of the vitreous fluid to prevent increases in intraocular pressure and leakage of the injected fluid through the opening formed by the delivery needle. More preferably, the volume injected is between about 10 and 200 μL. Most preferably, the volume for injection is between 30 and 100 μL, in particular about 50 μL.

With regard to the preferred routes of administration, the pharmaceutically acceptable salt, pharmaceutically acceptable solvate, isomer or mixture thereof is also an ophthalmically acceptable salt, ophthalmically acceptable solvate, isomer or mixture thereof. In a preferred embodiment, the pharmaceutical composition comprises the compound and one or more opthalmically acceptable carriers. Interestingly, compounds of the invention were found to have a high aqueous solubility of over 100 mg/ml, while prior art compounds have single digit mg/ml or lower aqueous solubilities. In a preferred embodiment, a composition of the invention as disclosed herein is an aqueous solution comprising a compound of the invention. In another embodiment, the present invention provides a kit of parts comprising a container comprising a compound of the invention and another container comprising an aqueous buffer for dissolving the compound of the invention.

As will be understood to the skilled person, a composition as disclosed herein is preferably a sterile composition. In a particular embodiment, the present invention provides a sterile container comprising a compound or composition of the invention. In a further embodiment, the sterile container is a vial comprising a compound or composition of the invention. The vial may comprise the compound as a powder or as a solution, preferably an aqueous solution. In a more particular embodiment, the present invention provides a sterile vial comprising an aqueous solution of the compound of the invention. In an even more particular embodiment, a vial as described herein comprises a part that is designed to be pierceable by a syringe needle. In alternative embodiment, the present invention provides a kit comprising a vial with the compound of the invention in a powder form and a container comprising an aqueous solution, particularly an aqueous buffer solution. In another embodiment, the sterile container is a syringe prefilled with a pharmaceutical composition of the invention, particularly an aqueous solution comprising the compound of the invention. In yet another embodiment, the sterile container is a container comprising at least one tablet comprising a pharmaceutical composition of the invention. In particular a blister package or bottle comprising multiple tablets comprises a compound of the invention and one or more pharmaceutically acceptable carriers. In one particular embodiment, a vial as described comprises less than 5 mL, in particular less than 4 mL, more in particular less than 3 mL of a solution comprising the compound of the invention.

In a preferred embodiment, the present invention further relates to the compound for use, wherein the treatment, inhibition and/or prevention of the previously mentioned disorders further comprises administering a compound that binds to and inhibits the activity of VEGF or a VEGF receptor. This compound can be a VEGF inhibitor, a VEGF receptor antibody or an antigen-binding fragment thereof, or a VEGF antibody or an antigen-binding fragment thereof. Suitable examples of such compounds include bevacizumab, ranibizumab, brolucizumab or conbercept. Another possible further compound is a VEGF trap, comprising a VEGF binding domain, such as aflibercept.

The present invention further relates to a combination comprising the compound of the present invention and a further compound that binds to and inhibits the activity of VEGF or a VEGF receptor. As specified above, this further compound can be a VEGF inhibitor, a VEGF receptor antibody or an antigen-binding fragment thereof, or a VEGF antibody or an antigen-binding fragment thereof such as bevacizumab, ranibizumab, brolucizumab or conbercept. Another possible further compound is a VEGF trap, comprising a VEGF binding domain, such as aflibercept.

Whenever reference is made to a combination of active ingredients, the active ingredients can be provided in a single composition or in separate composition. In addition, a combination of active ingredients also encompasses active ingredients that are linked non-covalently or covalently.

The present invention further relates to a combination as specified above for use as a medicament or to inhibit, treat and/or prevent pathological neovascularization, cancer or an ophthalmic disorder such as wet age-related macular degeneration, retinal detachment, posterior uveitis, corneal neovascularization, iris neovascularization, diabetic macular edema, and diabetic retinopathy.

The present invention also provides a method for antagonizing an integrin, in particular a vitronectin receptor, in a subject in need thereof, the method comprising administering the compound of the invention. More in particular, the invention provides methods for inhibiting angiogenesis in a subject. The present invention further relates to a method for inhibiting (pathological) neovascularization in a subject in need thereof, the method comprising administering the compound of the present invention. In a further embodiment, the present invention provides a method for inhibiting ocular neovascularization in a subject, the method comprising administering a compound of the invention to the subject. In yet another particular embodiment, method comprises administration of the compound or composition of the invention to the eye of a subject, such as by intravitreal injection. In particular, the method comprises intravitreal injection of a composition as described herein.

The present invention further provides the compounds and compositions described herein for use in the manufacture of a medicament for the prevention and/or treatment of a disorder as described herein.

EXAMPLES

Example 1—Synthesis of the Compounds of the Invention

Synthesis of benzyl N-[(2S)-1-(tert-butoxy)-3-({2,5-dimethyl-6-[4-(1,8-naphthyridin-2-yl)piperidin-1-yl]pyrimidin-4-yl}amino)-1-hydroxypropan-2-yl]carbamate

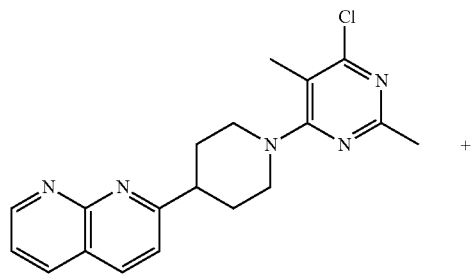

+

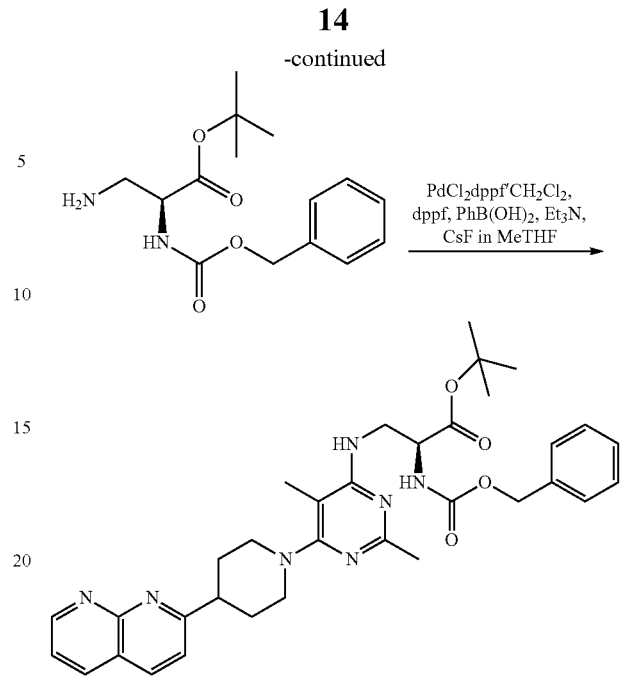

2-[1-(6-chloro-2,5-dimethylpyrimidin-4-yl)piperidin-4-yl]-1,8-naphthyridine and tert-butyl (2S)-3-amino-2-{[(benzyloxy)carbonyl]amino}propanoate were prepared in accordance with the method described in US2008/0058348 A1, which is herewith incorporated by reference. Both molecules were coupled in a Buchwald-Hartwig amination reaction catalyzed by dichloro[1,1'-bis(diphenylphosphino)ferrocene]palladium(II) dichloromethane complex (1:1), 1,1'-ferrocenediyl-bis diphenylphosphine, phenylboronic acid, triethylamine and cesium fluoride in 2-methyltetrahydrofuran. The reaction mixture was filtered through celite and extracted with aqueous hydrochloric acid. The aqueous extract was neutralized with aqueous sodium acetate and extracted with dichloromethane which was washed with aqueous sodium bicarbonate and dried over sodium sulfate to give the crude product which was purified by column chromatography on silica using toluene/ethyl acetate as eluent. The chromatographed material was dissolved in ethyl acetate and further purified by crystallization as the (−)-dibenzoyl-L-tartaric acid salt. Using aqueous sodium bicarbonate the tartaric acid salt was removed to give the purified product.

Synthesis of tert-butyl (2S)-2-amino-3-({2,5-dimethyl-6-[4-(5,6,7,8-tetrahydro-1,8-naphthyridin-2-yl)piperidin-1-yl]pyrimidin-4-yl}amino)propanoate

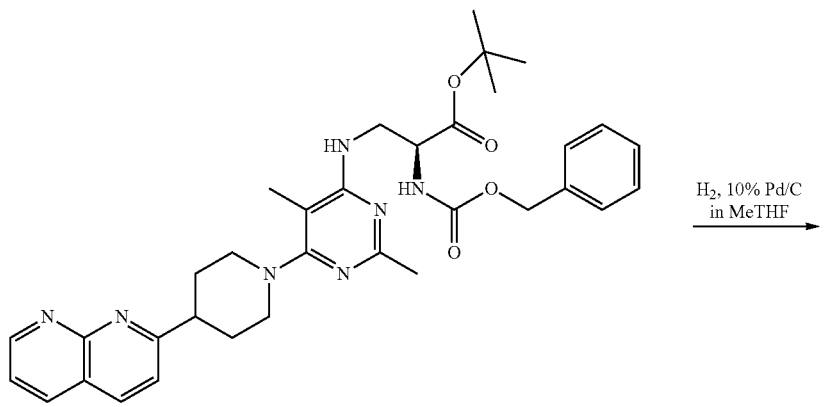

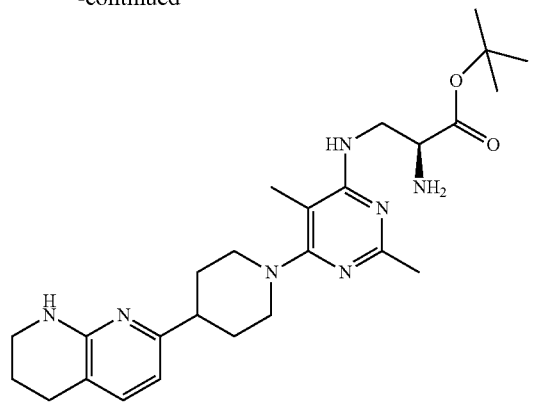

Benzyl N-[(2S)-1-(tert-butoxy)-3-({2,5-dimethyl-6-[4-(1,8-naphthyridin-2-yl)piperidin-1-yl]pyrimidin-4-yl}amino)-1-hydroxypropan-2-yl]carbamate was hydrogenated over palladium on activated carbon in 2-methyltetrahydrofuran. The catalyst was removed by filtration through celite. The solvent was evaporated off to give the desired product Synthesis of tert-butyl (2S)-3-({2,5-dimethyl-6-[4-(5,6,7,8-tetrahydro-1,8-naphthyridin-2-yl)piperidin-1-yl]pyrimidin-4-yl}amino)-2-{[(3-methoxy-3-oxo-propoxy)carbonyl]amino}npropanoate

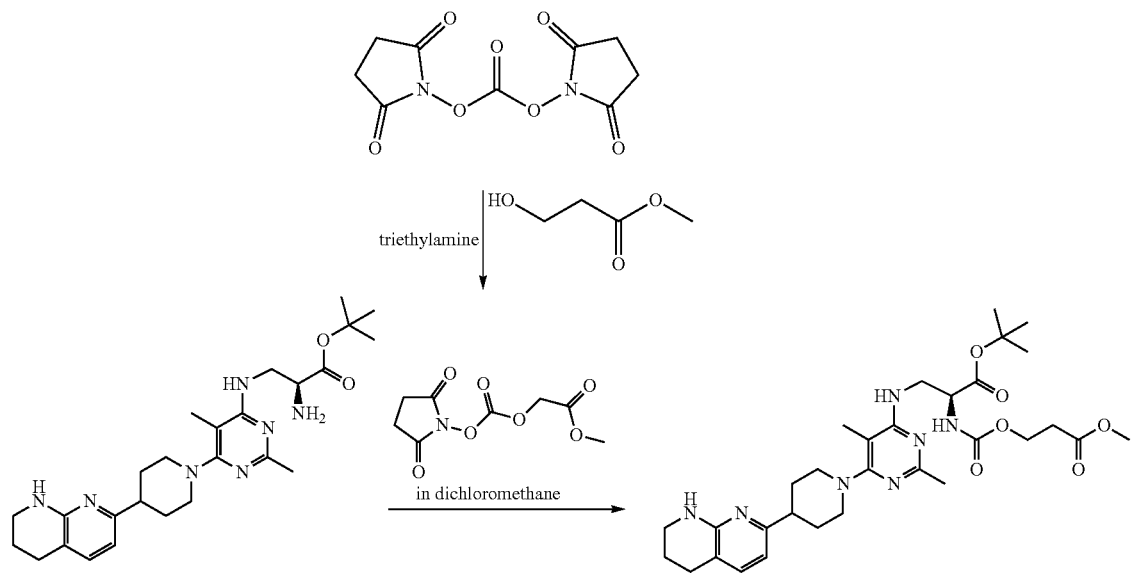

N,N-disuccinimidyl carbonate was reacted, in the presence of triethylamine, with methyl 3-hydroxypropanoate in dichloromethane to give methyl 2-({[(2,5-dioxopyrrolidin-1-yl)oxy] carbonyl}oxy)acetate. Tert-butyl (2S)-2-amino-3-({2,5-dimethyl-6-[4-(5,6,7,8-tetrahydro-1,8-naphthyridin-2-yl)piperidin-1-yl]pyrimidin-4-yl}amino)propanoate was added to give the desired product. The reaction mixture was washed with aqueous hydrochloric acid and aqueous sodium bicarbonate and then dried over sodium sulfate to give the crude product which was purified by column chromatography on silica using ethyl acetate/n-heptane/triethylamine as eluent.

Synthesis of (2S)-3-({2,5-dimethyl-6-[4-(5,6,7,8-tetrahydro-1,8-naphthyridin-2-yl)piperidin-1-yl]pyrimidin-4-yl}amino)-2-{[(3-methoxy-3-oxopropoxy)carbonyl]amino}propanoic acid trifluoro acetate

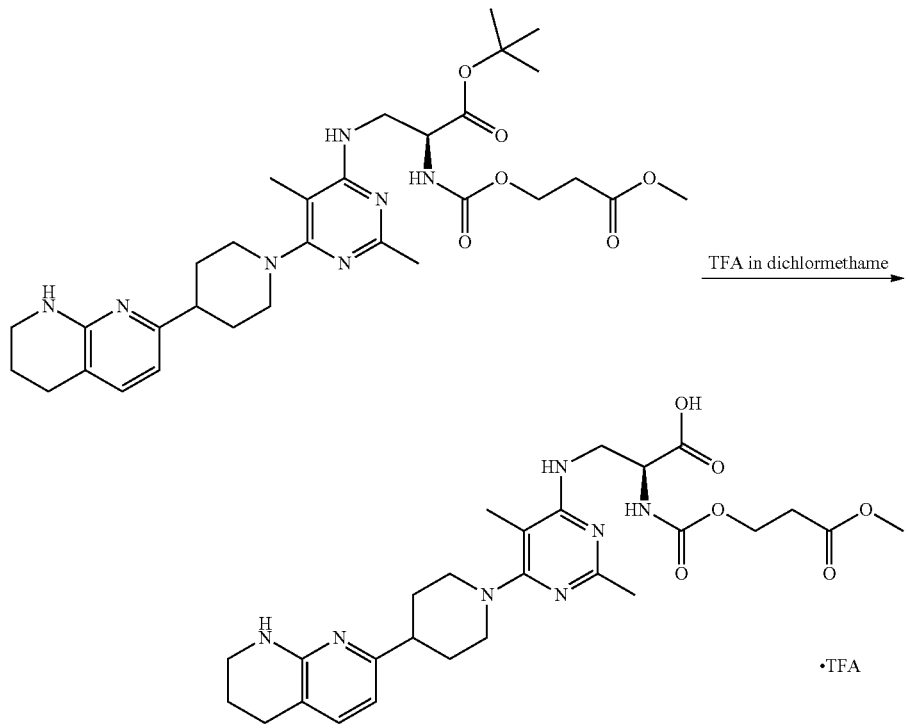

Tert-butyl (2S)-3-({2,5-dimethyl-6-[4-(5,6,7,8-tetrahydro-1,8-naphthyridin-2-yl)piperidin-1-yl]pyrimidin-4-yl)}amino)-2-{[(2-methoxy-2-oxoethoxy)carbonyl]amino}propanoate was dissolved in dichloromethane and treated with trifluoracetic acid. The reaction mixture was washed brine and the solvent evaporated off to give the desired product as a trifluoracetic acid salt. The resulting compound is further referred to as comparative compound A (cpd A).

Electron Spray (ES) low resolution MS m/z: 556 [(M+1), 100%]

Synthesis of (2S)-2-{[(2-carboxyethoxy)carbonyl]amino}-3-({2,5-dimethyl-6-[4-(5,6,7,8-tetrahydro-1,8-naphthyridin-2-yl)piperidin-1-yl]pyrimidin-4-yl}amino)propanoic acid

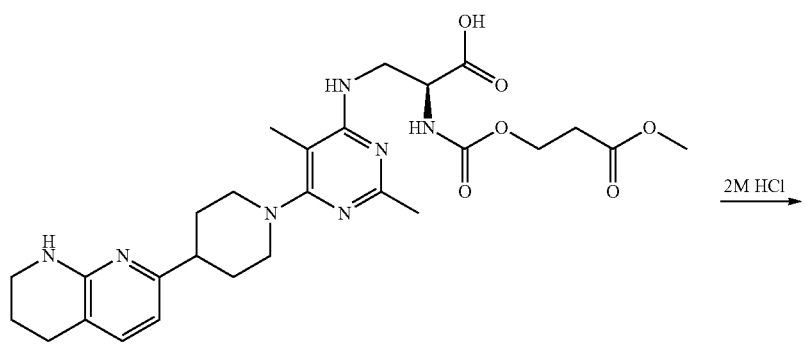

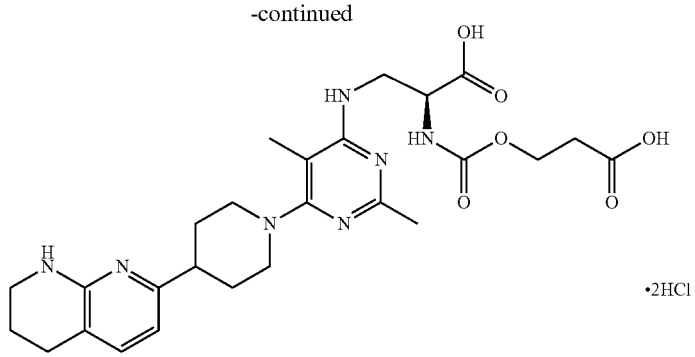

(2S)-3-({2,5-dimethyl-6-[4-(5,6,7,8-tetrahydro-1,8-naphthyridin-2-yl)piperidin-1-yl]pyrimidin-4-yl}amino)-2-{[(3-methoxy-3-oxopropoxy)carbonyl]amino}propanoic acid trifluoro acetate is dissolved in 2M aqueous hydrochloric acid. After completion of the reaction the solvent is lyophilized off the give the desired product. (2S)-2-{[(2-carboxyethoxy)carbonyl]amino}-3-({2,5-dimethyl-6-[4-(5,6,7,8-tetrahydro-1,8-naphthyridin-2-yl)piperidin-1-yl]pyrimidin-4-yl}amino)propanoic acid, is further referred to as compound 1 (cpd1).

Electron Spray (ES) low resolution MS m/z: 542 [(M+1), 100%]

Synthesis of tert-butyl (2S)-2-({[2-(tert-butoxy)-2-oxoethoxy]carbonyl}amino)-3-({2,5-dimethyl-6-[4-(5,6,7,8-tetrahydro-1,8-naphthyridin-2-yl)piperidin-1-yl]pyrimidin-4-yl}amino)propanoate

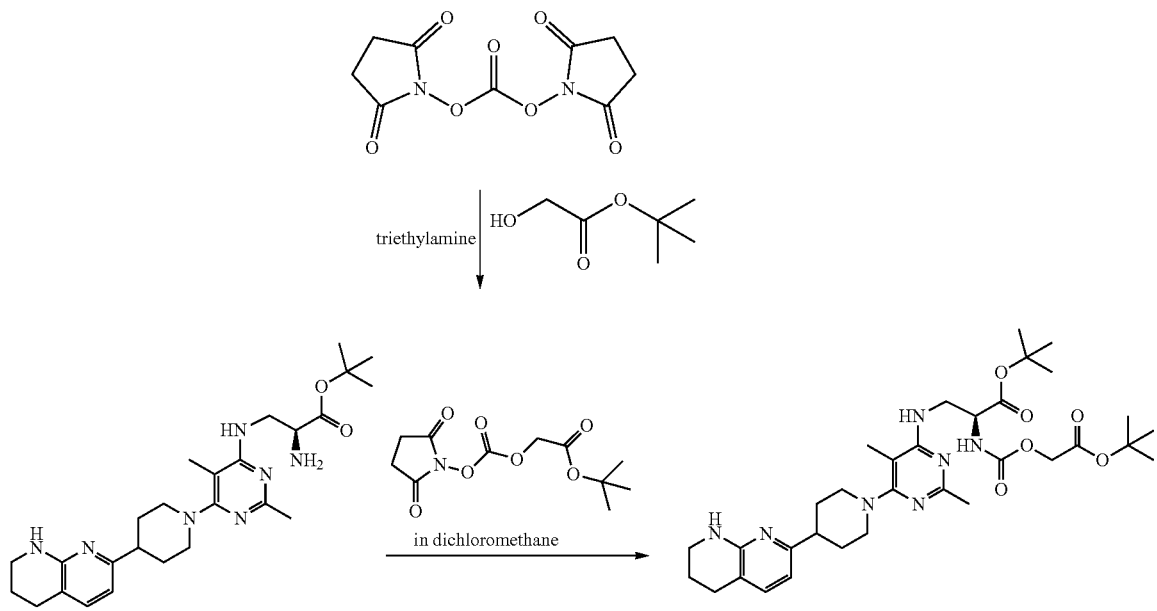

N,N-disuccinimidyl carbonate was reacted, in the presence of triethylamine, with tert-butyl 2-hydroxyacetate in dichloromethane to give tert-butyl 2-({[(2,5-dioxopyrrolidin-1-yl)oxy] carbonyl}oxy)acetate. Tert-butyl (2S)-2-amino-3-({2,5-dimethyl-6-[4-(5,6,7,8-tetrahydro-1,8-naphthyridin-2-yl)piperidin-1-yl]pyrimidin-4-yl}amino) propanoate was added. After completion of the reaction the reaction mixture was washed with aqueous hydrochloric acid and aqueous sodium bicarbonate and then dried over sodium sulfate to give the crude product. The crude product was purified by column chromatography on silica using ethyl acetate/n-heptane/triethylamine as eluent.

Synthesis of (2S)-2-([[(carboxymethoxy)carbonyl]amino)-3-({2,5-dimethyl-6-[4-(5,6,7,8-tetrahydro-1,8-naphthyridin-2-yl)piperidin-1-yl]pyrimidin-4-yl}amino)propanoic acid dihydrochloride (THR-687)

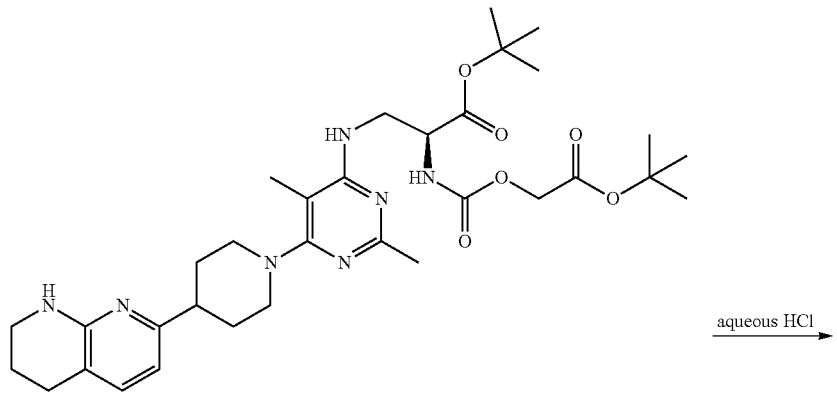

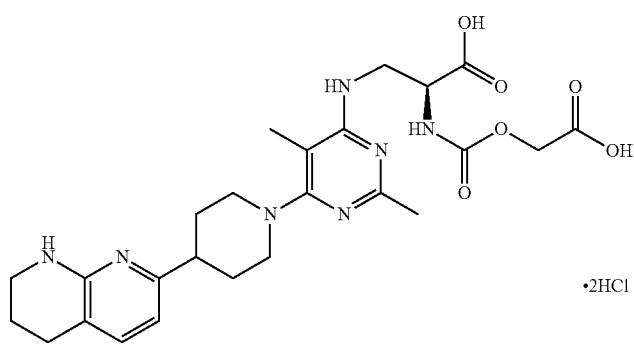

Tert-butyl (2S)-2-({[2-(tert-butoxy)-2-oxoethoxy]carbonyl}amino)-3-({2,5-dimethyl-6-[4-(5,6,7,8-tetrahydro-1,8-naphthyridin-2-yl)piperidin-1-yl]pyrimidin-4-yl}amino)propanoate was hydrolyzed with aqueous hydrochloric acid. The reaction mixture is washed with n-heptane to give compound 2 (cpd2) upon evaporation.

$^1$H NMR (400 MHz, DMSO-d$_6$) δ: 7.64 (d 1H), 6.71 (d 1H), 4.63 (d 1H), 4.46 (d 1H), 4.57 (dd 1H), 4.06 (dd 1H), 3.85 (dd 1H), 3.77 (m 2H), 3.53 (dd 2H), 3.27 (m, 2H), 3.01 (tt 1H), 2.84 (dd 2H), 2.58, (s 3H), 2.10 (dd, 2H), 2.07, (s 3H), 1.99 (t, 2H), 1.95 (td 2H)

Synthesis of tert-butyl (2S)-3-({2,5-dimethyl-6-[4-(5,6,7,8-tetrahydro-1,8-naphthyridin-2-yl)piperidin-1-yl]pyrimidin-4-yl}amino)-2-({[(1-ethoxy-1-oxopropan-2-yl)oxy]carbonyl}amino)propanoate

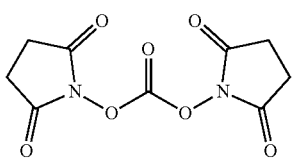

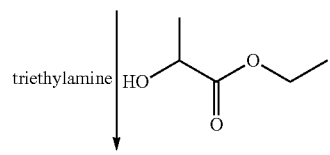

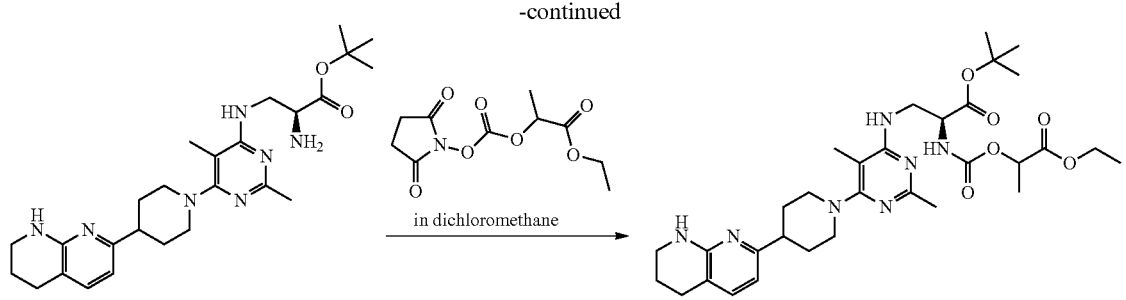

N,N-disuccinimidyl carbonate was reacted, in the presence of triethylamine, with ethyl 2-hydroxypropanoate in dichloromethane to give ethyl 2-({[(2,5-dioxopyrrolidin-1-yl)oxy]carbonyl}oxy)propanoate. Tert-butyl (2S)-2-amino-3-({2,5-dimethyl-6-[4-(5,6,7,8-tetrahydro-1,8-naphthyridin-2-yl)piperidin-1-yl]pyrimidin-4-yl}amino)propanoate was added. After completion of the reaction the reaction mixture was washed with aqueous hydrochloric acid and aqueous sodium bicarbonate and then dried over sodium sulfate to give the crude product. The crude product was purified by column chromatography on silica using dichloromethane/methanol as eluent.

Synthesis of (2S)-2-{[(1-carboxyethoxy)carbonyl]amino}-3-({2,5-dimethyl-6-[4-(5,6,7,8-tetrahydro-1,8-naphthyridin-2-yl)piperidin-1-yl]pyrimidin-4-yl}amino)propanoic acid, dihydrochloride

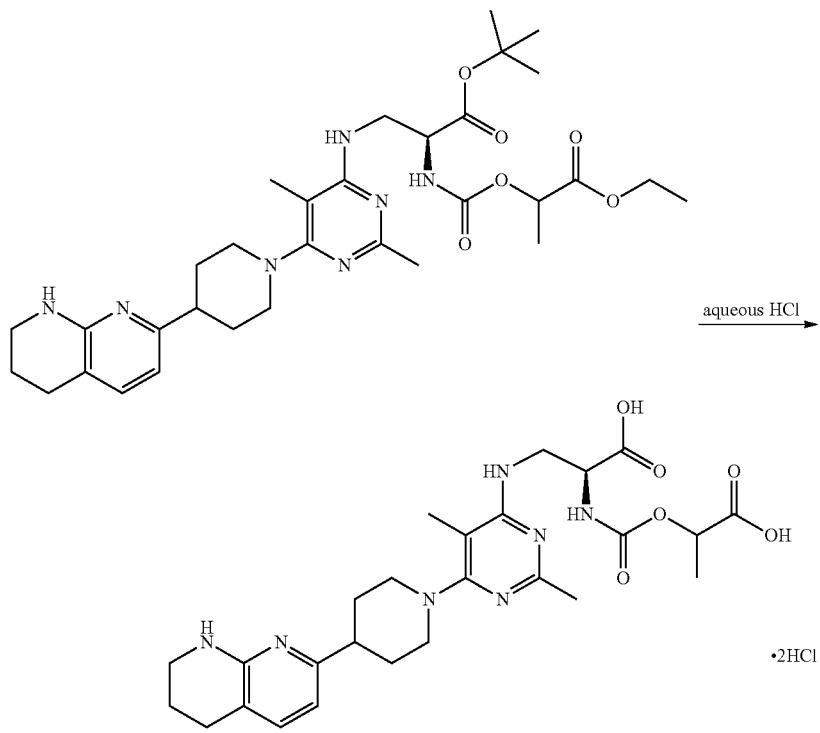

Tert-butyl (2S)-3-({2,5-dimethyl-6-[4-(5,6,7,8-tetrahydro-1,8-naphthyridin-2-yl)piperidin-1-yl]pyrimidin-4-yl}amino)-2-({[(1-ethoxy-1-oxopropan-2-yl)oxy]carbonyl}amino)propanoate was hydrolyzed with aqueous hydrochloric acid. The reaction mixture is washed with n-heptane to give the product upon evaporation, further referred to as compound 3 (cpd3).

$^1$H NMR (400 MHz, D$_2$O) δ: 7.5 (d 1H), 6.5 (d 1H), 4.5 (m 1H), 4.2 (m 1H), 3.9 (dd 1H), 3.5-3.7 (m 3H), 3.4 (t 2H), 3.1 (t 2H), 2.8 (m 1H), 2, 7 (t 2H), 2.4 (s 3H), 1.9 (s 3H), 1.9-2.0 (m 3H), 1.7-1.9 (m 4H), 1.3 (d 3H).

Accordingly, the following compounds of the invention have been made:
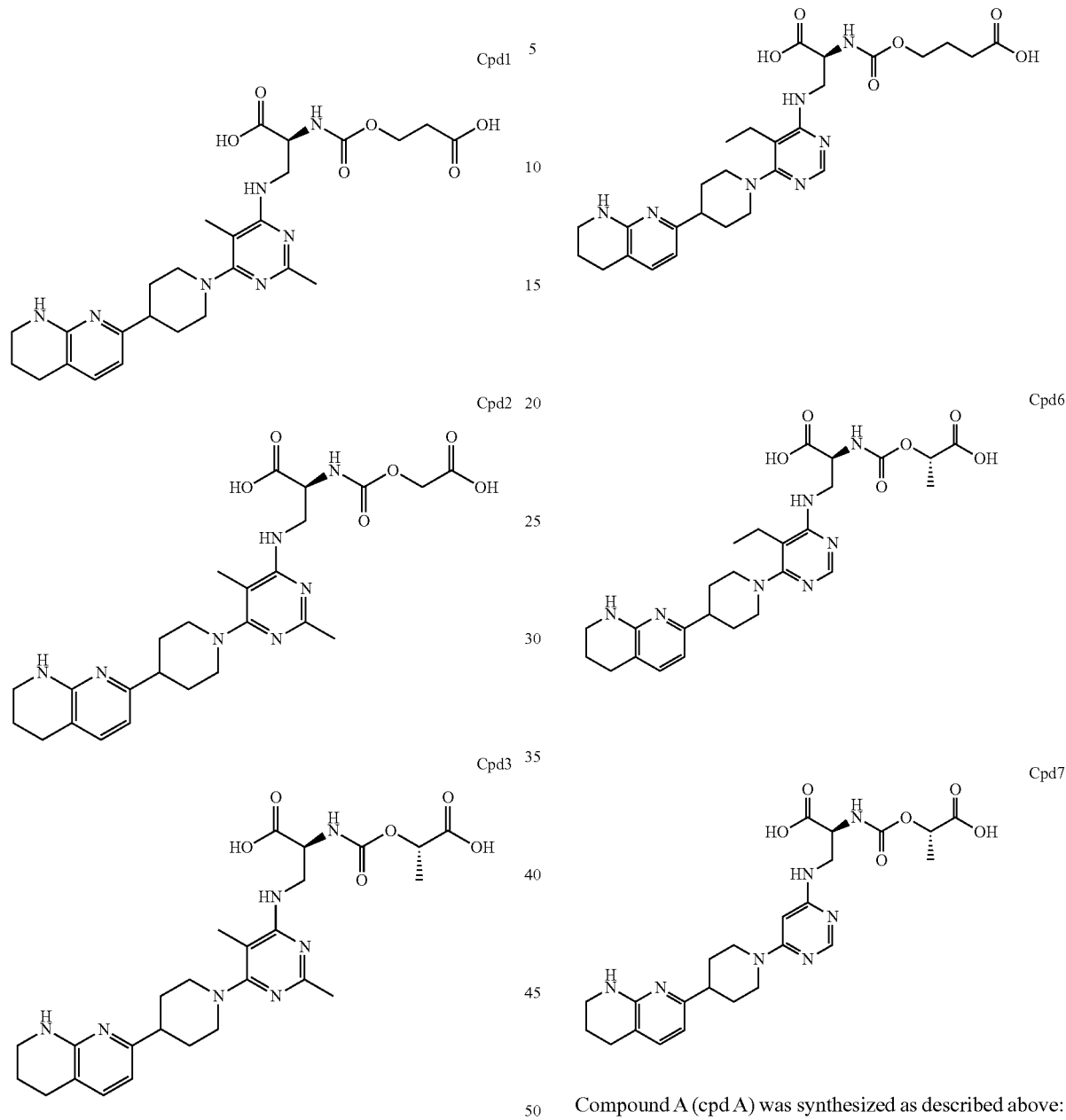
Other exemplary compounds according to the invention are:
Compound A (cpd A) was synthesized as described above:
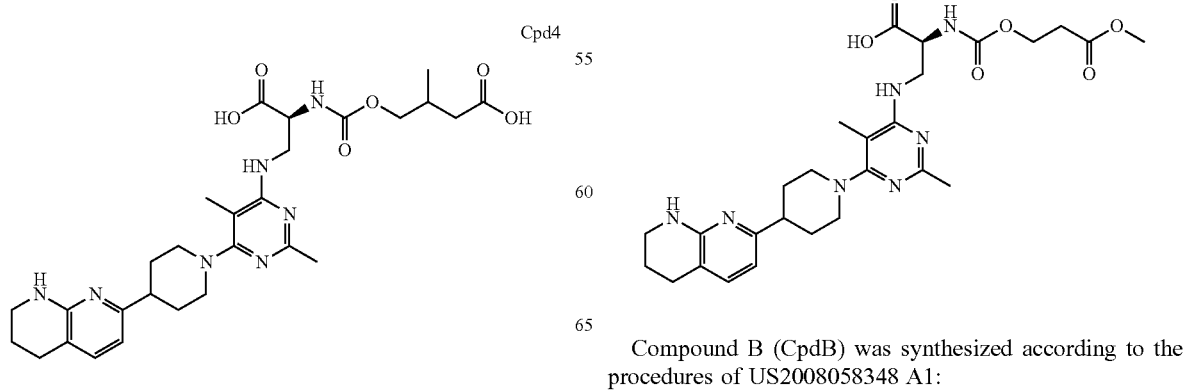
Compound B (CpdB) was synthesized according to the procedures of US2008058348 A1:

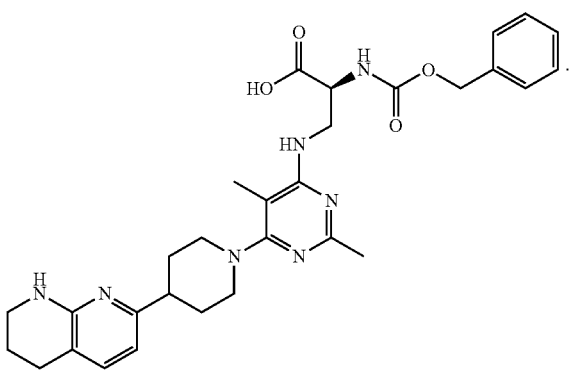 [SMILES: Cc1nc(NC[C@H](NC(=O)OCc2ccccc2)C(=O)O)c(C)c(N2CCC(c3ccc4c(n3)NCCC4)CC2)n1]

Example 2—Integrin Antagonism

The principle of the competition ELISA assays used here was as follows: (1) the integrin receptor under investigation was coated to 96-well plates and the wells were blocked, (2) an integrin ligand (fibronectin) was then added to the relevant wells in the presence of increasing concentrations of a given integrin antagonist, (3) after a defined amount of time, the wells were washed and the bound ligand was detected with the help of a specific reagent. Quantitative analysis of the data was then performed to determine EC50 values, i.e. the concentration of the integrin antagonist that reduces ligand binding to the coated receptor by 50%.

TABLE 1

EC50 for the different integrins and human integrin antagonists.

|      | $\alpha_v\beta_3$ | $\alpha_v\beta_5$ | $\alpha_5\beta_1$ | $\alpha_{IIb}\beta_3$ |
|------|------|------|------|------|
| cpd1 | +++ | +++ | +++ | + |
| cpd2 | +++ | +++ | +++ | + |
| cpd3 | +++ | +++ | +++ | + |
| cpdA | +++ | +++ | +++ | +++ |
| cpdB | ++  | +++ | +++ | +++ |

+++: between 1 and 10 nM;
++: between 10 and 25 nM;
+: >25 nM

The compound according to formula (I) inhibits interactions between integrins and their ligands. The compound according to formula (I) has been shown to antagonize several integrin receptors, including $\alpha_v\beta_3$, $\alpha_v\beta_5$ and $\alpha_5\beta_1$, with single-digit nanomolar affinity. These integrin receptors have been shown to play a role in angiogenesis $\alpha_v\beta_3$, $\alpha_v\beta_5$ and $\alpha_5\beta_1$), vascular permeability ($\alpha_v\beta_3$ and $\alpha_v\beta_5$) and vitreoretinal adhesion ($\alpha_5\beta_1$).

Notably, compounds of the invention show a significantly reduced antagonism towards the platelet integrin $\alpha_{IIb}\beta_3$, which is involved in platelet aggregation. FIG. 1 sets forth the determined ratios of EC50 values for $\alpha_v\beta_3$ over $\alpha_{IIb}\beta_3$. As derivable from these results, compounds of the present invention show a much lower activity towards the platelet integrin compared to the $\alpha_v\beta_3$ integrin. In contrast, compounds as described in the prior art show a significantly higher activity towards the platelet integrin compared to the $\alpha_v\beta_3$ integrin.

Example 3—Cell Migration Assay

Endothelial cell wound healing is mediated by endothelial cell migration and proliferation, both critical components of the angiogenesis process, and is routinely used as a surrogate model for in vitro angiogenic potential. The ORIS™ Cell Migration Assay was used with human umbilical vein endothelial cells (HUVECs).

HUVEC cells (SCCE-001, Cat no 1000519, Merck Chemicals) were cultured in T175 flasks (Cat no 353112, falcon) in EndoGro Growth Medium (SCME-003, Merck Chemicals) and split when they reached 90-100% confluence.

For the assay, cells were used at passage 2 to 4 after thawing and at 80-90% confluency. At the beginning of the day, the fibronectin-coated Oris™ Cell Migration Assay Plates (Cat no # CMAFN.101, AMS Biotechnology) were removed from refrigeration and placed at RT for 1 h. The Oris Detection Masks were washed with ethanol and applied to the bottom of the 96-well plates, aligning the A1 corner of the masks with the A1 corner of the plates. Cells were harvested by trypsinization (Cat no 25300, Gibco), centrifuged at 250 g for 5 mm and suspended at $0.4 \cdot 10^6$ per mL in complete EndoGro growth medium. 100 μL of the cell suspension were added to the wells and the plates were incubated for 6 h at 37° C. and 5% C02 to allow cells to adhere.

At the end of the incubation, the stopper tool was washed with ethanol and used to remove the stoppers from all the wells except the reference wells. 100 μL of growth medium containing different concentrations of the compounds (cpd2, cpd3, cpdB, cilengitide) were added to the wells and the plates were transferred for 24 h to the incubator at 37° C. and 5% $CO_2$ to allow migration.

Just prior to the end of the incubation, a 4 μg/mL calcein AM (Cat no 354217, Beckton Dickinson) solution was prepared in pre-warmed HBSS (Cat no 14025, Gibco). The stoppers were removed from the reference wells and the medium was carefully removed from all the wells with a multichannel (no vacuum aspiration). The wells were washed with 100 μL DPBS. Then, 100 μL of the calcein AM solution were added and the plates were incubated for 1 hour at 37° C. and 5% $CO_2$. After incubation the fluorescence was read at 494 nm excitation and 517 nm emission wavelengths using the Flexstation and the SofiMax Pro 5.4.5 software (Molecular Devices). The fluorescence was read from the bottom of the plates with the lid on to keep them sterile. The masks were then removed and pictures were taken with the Axiovert fluorescence microscope (Zeiss) using reflected light, GFP and a 2.5× objective.

IC50 values for cpdB, cpd2 and cpd3 were all below 1 μM. IC50 for the positive control Cilengitide was 100 μM. It can be concluded that the compounds of Formula (I) retain strong activity and inhibit cell migration with IC50 values in the nanomolar range.

Example 4—Murine Choroidal Explant Assay

The assay is based on a murine microvascular angiogenesis explant model, which closely mimics in viva choroidal angiogenesis. The major advantage of this organotypical culture model is that cells are kept within their normal environment, thereby preserving cell-cell interactions, while maintaining a higher level of experimental control than in animal models. The choroidal explant model or briefly EMCA model allows for rapid evaluation of new anti-angiogenic therapeutics, with the additional benefit of excluding the potential lack of exposure often encountered when testing small molecules in animal eyes. RPE-choroid sclera explants (hereinafter referred to as choroid explants) are embedded in a three-dimensional fibrinogen/fibrin gel. Addition of serum-containing medium induces extensive endothelial cell sprout outgrowth into the matrix after 3 to 4 days in culture.

Animals

All experiments were performed using 4 to 5-weeks old male C57BL/6J mice (Charles River Laboratories France), housed under standard laboratory conditions according to a normal day/night rhythm with ad libitum access to food and water. All animal experiments were approved by the Institutional Ethical Committee of KU Leuven.

Dissection of Choroid Tissue and Explant Culture Preparation

After initial optimization, a general protocol was set-up. Briefly, after euthanasia of the mice using pentobarbital (200 mg/kg, IP, Dolethal, Vetoquinol) followed by cervical dislocation, eyes were immediately enucleated with curved forceps and kept in ice-cold DPBS (cat no 14190-136, Gihco). Under a stereomicroscope, the eye was placed in a drop of ice-cold DPBS, and held in place with forceps on an ice-cold petri dish. The cornea and lens were removed via a circumferential incision at the limbus (cornea-sclera boundary) using Vannas spring scissors (Fine Science Tools). Next, redundant muscles were removed from the remaining eyeball and a cut was made from the edge of the posterior chamber towards the optic nerve head. After careful separation of the RPE-choroid-sclera complex from the retina, 6 to 8 explants were made at the periphery of this complex using a punch needle (750 µm diameter, Mediquip Surgical). Explants were transferred to a 48-well plate (BD Biosciences), prefilled with 350 µl serum-free DMEM (cat no 11995-065, Gibco) and 1% (v/v) Pen/Strep (cat no 15140-122, Gibco), and were incubated overnight at 37° C. in 5% CO2.

Choroid Explant Embedding in Fibrinogen/Fibrin Gel and Culture Conditions

Bovine fibrinogen (3.1 mg/mi, cat no F863, Sigma-Aldrich) was dissolved in DMEM (cat no 11995-065, Gibco) containing 1% (v/v) Pen/Strep (cat no 15140-122, Gibco), and subsequently filtered through a 0.22 µm pore filter (Corning). Next, 10 µg/mL of the serine protease inhibitor aprotinin (cat no A6279, Sigma-Aldrich) was added to the fibrinogen solution in order to block fibrinolytic activity. Following addition of 400 mU/mL of bovine thrombin (SRP6555, Sigma-Aldrich), this fibrinogen-aprotinin-thrombin solution was quickly dispensed into 48-well plates (100 µL per well), and allowed to solidify at 37° C. for at least 5 mm. On top of the fibrin-coated wells, 175 µL of fibrinogen plus aprotinin solution was added, followed by transfer of individual RPE-choroid explants in 175 µL DMEM medium using a cut tip. Finally, 1.4 µL of thrombin (400 mU/nit) was added to each well and this mixture was allowed to gel at 37° C. and 5% $CO_2$ for 1 hr. After clotting, 350 µL of DMEM containing 10% FBS (SH30071.03, heat-inactivated. HyClone) and the molecule(s) under test (cpd3, cpdB and cilengitide) were added on top of the gel and plates were incubated at 37° C. in 5% $CO_2$.

Quantification of Vessel Sprouting

After 3 to 4 days, bright field pictures were taken at 2.5× magnification with the Axio Vert.A1 inverted microscope (Zeiss) using ZEN lite 2012 microscope software (Zeiss). Analysis of the vessel outgrowth area was performed manually on ZVI images, more specifically by outlining the explant body, as well as the total vessel outgrowth area (including the explant body) using Axiovision Rel 4.8 software ("Measure>Outline", Zeiss). Further analysis was performed in Microsoft Excel, where the sprouting area of endothelial organotypic culture was quantified by subtracting the area of the tissue explant from the total area occupied by the sprouts. As absolute sprouting areas between independent experiments are slightly different, all data within each experiment were normalized to the vehicle-treated condition and IC50 values were calculated (GraphPad Prism 5).

Results

Figure 2:
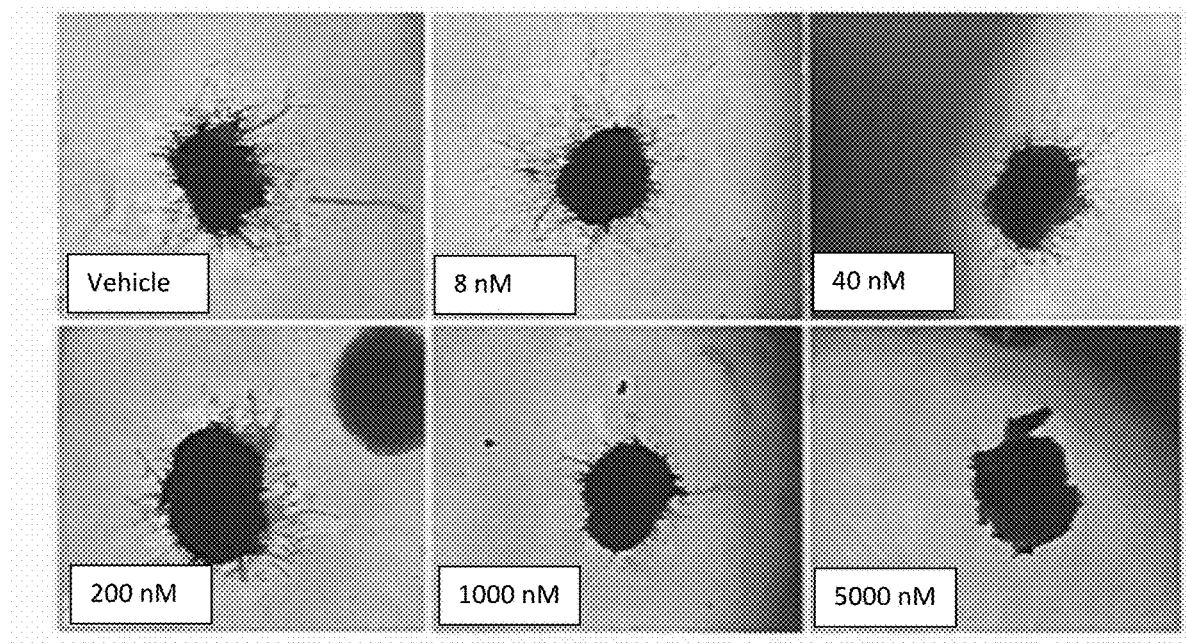
FIG. 2 Shows the inhibition of vessel sprouting by cpd3 in a murine choroidal explant assay.

All integrin antagonists blocked endothelial sprout formation in a concentration dependent manner. This is in line with studies showing that endothelial cells can associate with fibrinogen via ROD recognition specificity. Indeed, fibrinogen contains multiple binding sites for $\alpha_v\beta3$ and $\alpha5\beta1$ integrins, known to be expressed by endothelial cells and important regulators of (pathological) angiogenesis. Cpd3 and CpdB inhibited vessel outgrowth with $IC_{50}$ values around 1 µM, while for the positive control Cilengitide, the measured $IC_{50}$ was around 300 µM. Representative bright field pictures for cpd3 are shown in FIG. 2. These findings are in line with the results of the cell migration assay, discussed in example 3.

In conclusion, the compounds of the present invention are pan-integrin inhibitors showing strong antagonism against multiple integrin receptors that have been shown to play a role in angiogenesis ($\alpha_v\beta_3$, $\alpha_v\beta_5$ and $\alpha_5\beta_1$), vascular permeability ($\alpha_v\beta_3$ and $\alpha_v\beta_5$) and vitreoretinal adhesion ($\alpha_5\beta_1$). On the other hand, in relation to comparative compounds, the compounds of the invention show a much lower antagonism of the platelet integrin ($\alpha_{IIb}\beta_3$), thereby reducing the risk of interfering with platelet aggregation and increasing the therapeutic window. Furthermore, it has been shown that the compounds of the invention inhibit cell migration and reduce vessel sprouting. The invention provides novel integrin antagonists that are useful for, amongst others, the treatment of neovascular diseases.

While illustrative embodiments have been illustrated and described, it will be appreciated that various changes can be made therein without departing from the spirit and scope of the invention.

The embodiments of the invention in which an exclusive property or privilege is claimed are defined as follows:

1. A compound according to formula (I), or a pharmaceutically acceptable salt thereof,

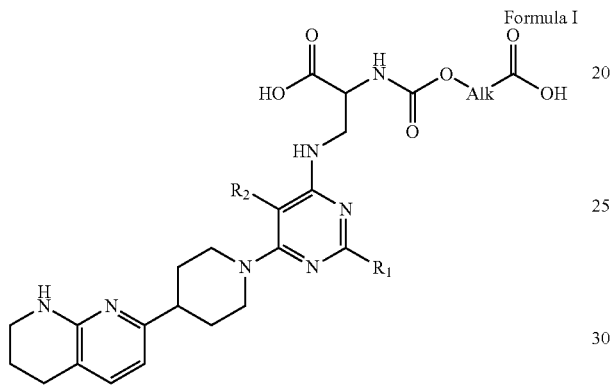

Formula I wherein $R_1$ and $R_2$ are independently selected from the group consisting of hydrogen, methyl and ethyl; and Alk is $C_{1-4}$alkylene.

2. The compound according to claim 1, wherein both $R_1$ and $R_2$ are methyl.

3. The compound according to claim 1, wherein Alk is a $C_1$ or $C_2$ alkylene.

4. The compound according to claim 1, wherein the compound is selected from the group consisting of:

5. A pharmaceutical composition comprising the compound according to claim 1, and one or more pharmaceutically acceptable carriers.

* * * * *